United States Patent
Winslow et al.

(10) Patent No.: US 11,324,426 B1
(45) Date of Patent: May 10, 2022

(54) SYSTEM, METHOD, AND COMPUTER PROGRAM PRODUCT FOR REAL-TIME EVALUATION OF PSYCHOLOGICAL AND PHYSIOLOGICAL STATES USING EMBEDDED SENSORS OF A MOBILE DEVICE

(71) Applicant: Design Interactive, Inc., Orlando, FL (US)

(72) Inventors: Brent Winslow, Kaysville, UT (US); Jeffrey A. Hullfish, Orlando, FL (US); Joanna Chiang, Torrance, CA (US)

(73) Assignee: DESIGN INTERACTIVE, INC., Orlando, FL (US)

(*) Notice: Subject to any disclaimer, the term of this patent is extended or adjusted under 35 U.S.C. 154(b) by 0 days.

(21) Appl. No.: 17/147,087

(22) Filed: Jan. 12, 2021

(51) Int. Cl.
*A61B 5/24* (2021.01)
*A61B 5/00* (2006.01)
(Continued)

(52) U.S. Cl.
CPC ............ *A61B 5/165* (2013.01); *A61B 5/1112* (2013.01); *A61B 5/1123* (2013.01);
(Continued)

(58) Field of Classification Search
CPC .......... A61B 5/0205; A61B 2562/0219; A61B 5/1118; A61B 5/1123; A61B 5/0002;
(Continued)

(56) References Cited

U.S. PATENT DOCUMENTS 9,384,321 B2 7/2016 Merel
9,420,970 B2 8/2016 Dagum
(Continued)

FOREIGN PATENT DOCUMENTS

WO 2014190230 11/2014
WO 2016096743 6/2016

OTHER PUBLICATIONS

Sano, A. et al. "Identifying Objective Physiological Markers and Modifiable Behaviors for Self-Reported Stress and Mental Health Status Using Wearable Sensors and Mobile Phones: Observational Study." J Med Internet Res 2018. https://www.jmir.org/2018/6/e210.

(Continued)

*Primary Examiner* — Christine H Matthews
*Assistant Examiner* — Joshua Daryl D Lannu
(74) *Attorney, Agent, or Firm* — Terry M. Sanks, Esquire; Beusse Sanks, PLLC

(57) ABSTRACT

A system including a mobile device with at least one sensor to collect data about a user based on movement of the user in possession of the mobile device, a movement feature analyzer configured to determine out-of-the-ordinary movement pattern made by the user, a physiological/psychological state classifier configured to classify a physiological/psychological state of the user based on the out-of-the-ordinary movement of the user based on the movement feature analyzer and report at least one of a magnitude and a level of the physiological/psychological state experienced by the user based on at least one of data collected about the motion experienced by the mobile device and data collected about the geographic location of the mobile device, and a notification device to provide notification that the user is experiencing a physiological/psychological state measured on the at least physiological/psychological state level and the physiological/psychological state magnitude.

22 Claims, 5 Drawing Sheets

(51) Int. Cl.

| | |
|---|---|
| *A61M 21/00* | (2006.01) |
| *G06V 40/00* | (2022.01) |
| *A61B 5/16* | (2006.01) |
| *G06K 9/00* | (2022.01) |
| *G06K 9/62* | (2022.01) |
| *G09B 19/00* | (2006.01) |
| *A61B 5/11* | (2006.01) |
| *A61M 21/02* | (2006.01) |

(52) U.S. Cl.
CPC .......... *A61B 5/4836* (2013.01); *A61B 5/6898* (2013.01); *A61B 5/7264* (2013.01); *A61B 5/742* (2013.01); *A61B 5/7405* (2013.01); *A61B 5/7455* (2013.01); *G06K 9/00335* (2013.01); *G06K 9/6277* (2013.01); *G09B 19/00* (2013.01); *A61B 5/7267* (2013.01); *A61M 21/02* (2013.01)

(58) Field of Classification Search
CPC ... A61B 5/024; A61B 5/4812; A61B 5/02055; A61B 5/021; A61B 5/4809; A61B 5/02007; A61B 5/14532; A61B 5/4815; A61B 5/7264; A61B 5/0816; A61B 5/02438; A61B 5/112; A61B 5/7278; A61B 17/0686; A61B 2560/0214; A61B 2560/0242; A61B 2560/0456; A61B 5/0004; A61B 5/1112; A61B 5/14546; A61B 5/222; A61B 5/4866; A61B 5/6801; A61B 5/6838; A61B 5/7405; A61B 5/743; A61B 5/744; A61B 5/7455; A61B 5/318; A61B 5/742; A61B 5/681; A61B 5/721; A61B 5/02416; A61B 5/0245; A61B 5/6824; A61B 5/02405; A61B 5/6831; A61B 5/746; A61B 5/11; A61B 5/163; A61B 5/369; A61B 5/18; A61B 5/6803; A61B 5/7225; A61B 5/0022; A61B 5/01; A61B 5/026; A61B 5/0261; A61B 5/1116; A61B 5/14552; A61B 5/168; A61B 5/291; A61B 5/4393; A61B 5/4818; A61B 5/4854; A61B 5/7203; A61B 5/726; A61B 5/7282; A61B 5/316; A61B 5/7267; A61B 5/0006; A61B 5/1122; A61B 5/332; A61B 5/4094; A61B 5/6802; A61B 5/6898; A61B 5/7246; A61B 2503/22; A61B 2560/0431; A61B 2562/043; A61B 5/00; A61B 5/0036; A61B 5/02444; A61B 5/05; A61B 5/053; A61B 5/1101; A61B 5/1102; A61B 5/1121; A61B 5/113; A61B 5/117; A61B 5/16; A61B 5/165; A61B 5/4806; A61B 5/4836; A61B 5/6885; A61B 5/6893; A61B 5/7221; A61B 5/7275
See application file for complete search history.

(56) References Cited

U.S. PATENT DOCUMENTS

| | | | |
|---|---|---|---|
| 9,474,481 | B2 | 10/2016 | Dagum |
| 9,538,948 | B2 | 1/2017 | Dagum |
| 9,693,724 | B2 | 7/2017 | Dagum |
| 10,748,644 | B2 | 8/2020 | Shriberg et al. |
| 2010/0203876 | A1 | 8/2010 | Krishnaswamy |
| 2013/0297536 | A1 | 11/2013 | Almosni et al. |
| 2015/0179079 | A1 | 6/2015 | Rodriguez, Jr. et al. |
| 2016/0089038 | A1* | 3/2016 | Chadderdon, III ........................ A61B 5/02055 600/301 |
| 2016/0128619 | A1* | 5/2016 | Geller ...................... A61B 5/11 600/595 |
| 2016/0373573 | A1 | 12/2016 | Bivens et al. |
| 2017/0277826 | A1 | 9/2017 | Ozerov et al. |
| 2019/0000384 | A1* | 1/2019 | Gupta .................. A61B 5/1123 |

OTHER PUBLICATIONS

Torous, J., Kiang, MV., Lorme, J., & Onnela, JP. "New Tools for New Research in Psychiatry: A Scalable and Customizable Platform to Empower Data Driven Smartphone Research." JMIR Ment Health 2016. https://mental.jmir.org/2016/2/e16.

Torous, J., Onnela, JP. & Keshavan, M. New dimensions and new tools to realize the potential of RDoC: digital phenotyping via smartphones and connected devices. Transl Psychiatry 7, e1053 (2017). https://doi.org/10.1038/tp.2017.25.

\* cited by examiner

SYSTEM, METHOD, AND COMPUTER PROGRAM PRODUCT FOR REAL-TIME EVALUATION OF PSYCHOLOGICAL AND PHYSIOLOGICAL STATES USING EMBEDDED SENSORS OF A MOBILE DEVICE

BACKGROUND

Embodiments relate to detecting psychological and physiological states of an individual and, more particularly, to a method and system for continuous classification of physiological and psychological states in when an individual is in motion using sensors of a mobile device.

Though mobile health applications and wearable physiological sensors have the potential to analyze and present meaningful data to better manage and optimize general health and specific health conditions of an individual, such applications currently simply collect data and produce readouts of the collected data. For example, wearable devices and mobile applications are now able to track fitness-related metrics such as, but not limited to, distance walked or run, calorie consumption, heartbeat rate, and quality of sleep.

Wearable physiological sensors provide quantifiable data in real-time that may correlate with stress (such as heart rate variability and electrodermal activity), but these sensors can be cumbersome and expensive.

There is a growing need to support the classification of physiological and psychological states when an individual is in a natural environment and movement of the individual in the natural environment, using data derived from ubiquitous sensors, such as a mobile device's sensors, including accelerometers, magnetometers, gyroscopes, global positioning systems (GPS), screen touches, gestures, cameras, application usage information, luxmeters, temperature, and Bluetooth encounters, among others. Detecting and addressing physiological and psychological states such as, but not limited to, stress, anxiety, anger, panic, or depression is a key measure for mobile health applications, but the main challenge in addressing this need is an inability to classify these states in a mobile environment in real-time, using mobile phone sensors. Current state of the art methods for physiological and psychological monitoring are laboratory-based (i.e., not mobile or able to be applied outside of a controlled environment) and episodic in nature (e.g., self-report). Therefore, individuals would benefit from a system and method that can actively, continuously and passively discriminate between adverse physiological and psychological states such as stress, anxiety, anger, panic, or depression and other (normal) physiological and psychological states of the user to provide an accurate, quantitative classifier for objective real-time stress assessment.

SUMMARY

Embodiments relate a computer-based method and system for to detecting psychological and physiological states of an individual when the individual is experiencing non-laboratory simulates stimuli. The system comprises a mobile device having a processor and a plurality of sensors, with at least one sensor as part of the mobile device, in communication with the mobile device configured to collect data about a user based on at least one of the plurality of sensors collecting information about movement of the user in possession of the mobile device. The system also comprises a movement feature analyzer configured to determine out-of-the-ordinary movement pattern made by the user based on at least one of data collected about a motion experienced by the mobile device and data collected about a geographic location of the mobile device, the movement feature analyzer comprises instructions which when executed by the processor causes the processor to determine temporal domain metrics and frequency domain metrics based on at least one of a mean, maximum, minimum, median, standard deviation, energy, skewness, amplitude, magnitude, kurtosis, and time duration of the data collected about the motion experience by the mobile device and the data collected about the geographic location of the mobile device. The system further comprises a physiological/psychological state classifier configured to classify a physiological/psychological state of the user based on the out-of-the-ordinary movement of the user based on the movement feature analyzer and report at least one of a magnitude and a level of the physiological/psychological state experienced by the user based on at least one of data collected about the motion experienced by the mobile device and data collected about the geographic location of the mobile device, the physiological/psychological state classifier comprises instructions which when executed by the processor causes the processor to apply prior results to newly collected data to classify the physiological/psychological state into at least one of the physiological/psychological state level and the physiological/psychological state magnitude. The system also comprises a notification device to provide at least one of an audible notification, a tactile notification and a visual notification that the user is experiencing a physiological/psychological state measured on the at least physiological/psychological state level and the physiological/psychological state magnitude, wherein the notifier further prompts the user to utilize at least one of a resource available within the mobile device and a technique to reduce the at least one of level and magnitude of adverse physiological/psychological state.

Another system comprises a mobile device having a processor and a plurality of sensors at least one of as part of the mobile device and in communication with the mobile device configured to collect data about a user based on at least one of the plurality of sensors collecting information about movement of the user in possession of the mobile device. The system also comprises a movement feature analyzer configured to an determine out-of-the-ordinary movement pattern made by the user based on at least one of data collected about a motion experienced by the mobile device and data collected about a geographic location of the mobile device, the movement feature analyzer comprises instructions which, when executed by the processor, causes the processor to determine temporal domain metrics and frequency domain metrics based on at least one of a mean, maximum, minimum, median, standard deviation, energy, skewness, amplitude, magnitude, kurtosis, and time duration of the data collected about the motion experience by the mobile device and the data collected about the geographic location of the mobile device. The system further comprises a behavior feature analyzer configured to determine behavior of the user based on at least one of data collected event logs captured by the mobile device and data collected about physical interactions of the user at a user interface of the mobile device, the behavior feature analyzer comprises instructions which, when executed by the processor, causes the processor to determine usage of the mobile device by the user based on event logs captured by the mobile device and user interaction with an input device of the mobile device to determine a behavior. The system also comprises an environmental feature analyzer configured to determine environmental information of where the mobile device is located, the environmental feature analyzer comprises instructions which, when executed by the processor, causes the processor to determine at least one of an ambient noise level, determine light level, determine weather conditions, and determine temperature. The system further comprises a physiological/psychological state classifier configured to classify the physiological/psychological state level based on the out-of-the-ordinary movement of the user based on the movement feature analyzer and report the physiological/psychological state level experienced by the user based on at least one of data collected about the motion experienced by the mobile device and data collected about the geographic location of the mobile device, the physiological/psychological state classifier comprises instructions which, when executed by the processor, causes the processor to apply prior results, based on behavior of the user determined by the event logs and physical interactions with the mobile device with instructions that, when executed by the processor, causes the processor to compare newly acquired information about mobile application usage based on the event logs and physical interactions of the user with the mobile device, and based on behavior of the user determined by the event logs and physical interactions with the mobile device with instructions that when executed by the processor causes the processor to compare newly acquired information about mobile application usage based on the event logs and physical interactions of the user with the mobile device, to newly collected data to classify physiological/psychological state into the physiological/psychological state level. The system further comprises a notification device to provide, in real-time, at least one of an audible notification, a tactile notification and a visual notification that the user is experiencing an adverse physiological/psychological state at a suprathreshold level, wherein the notifier further prompts the user to utilize at least one of a resource available within the mobile device and a technique to reduce the physiological/psychological state level.

The computer-based method comprises collecting data about a user when in possession of the mobile device based on a plurality of sensors within the mobile device that collects information about at least one of a movement of the user and a geographic location of the user. The computer-based method further comprises determining out-of-the-ordinary movement pattern made by the user based on at least one of data collected about a motion experienced by the mobile device and data collected about a geographic location of the mobile device, the movement feature analyzer comprises instructions which when executed by the processor causes the processor to determine temporal domain metrics and frequency domain metrics based on at least one of a mean, maximum, minimum, median, standard deviation, energy, skewness, amplitude, magnitude, kurtosis, and time duration of the data collected about the motion experience by the mobile device and the data collected about the geographic location of the mobile device. The computer-based method also comprises classifying a physiological/psychological state level based on the out-of-the-ordinary movement of the user based on the movement feature analyzer and report the physiological/psychological state level experienced by the user based on at least one of data collected about the motion experienced by the mobile device and data collected about the geographic location of the mobile device, the physiological/psychological state classifier comprises instructions which, when executed by the processor, causes the processor to apply prior results to newly collected data to classify physiological/psychological state into the physiological/psychological state level. The computer-based method further comprises notifying at least one of an audible notification, a tactile notification and a visual notification that the user is experiencing an adverse physiological/psychological state at a suprathreshold level, wherein the notifier further prompts the user to utilize at least one of a resource available within the mobile device and a technique to reduce the physiological/psychological state level.

In another embodiment, the computer-based method may reside on a non-transitory processor readable storage medium residing on the mobile device, providing an executable computer program product, the executable computer program product comprising a computer software code that, when executed on a processor, causes the processor to perform an embodiment of the steps disclosed above.

BRIEF DESCRIPTION OF THE DRAWINGS

A more particular description of embodiments briefly described above will be rendered by reference to specific embodiments thereof that are illustrated in the appended drawings. Understanding that these drawings depict only typical embodiments and are not therefore to be considered limiting of its scope, embodiments will be described and explained with additional specificity and details through the use of the accompanying drawings in which.

DETAILED DESCRIPTION

Figure 1:
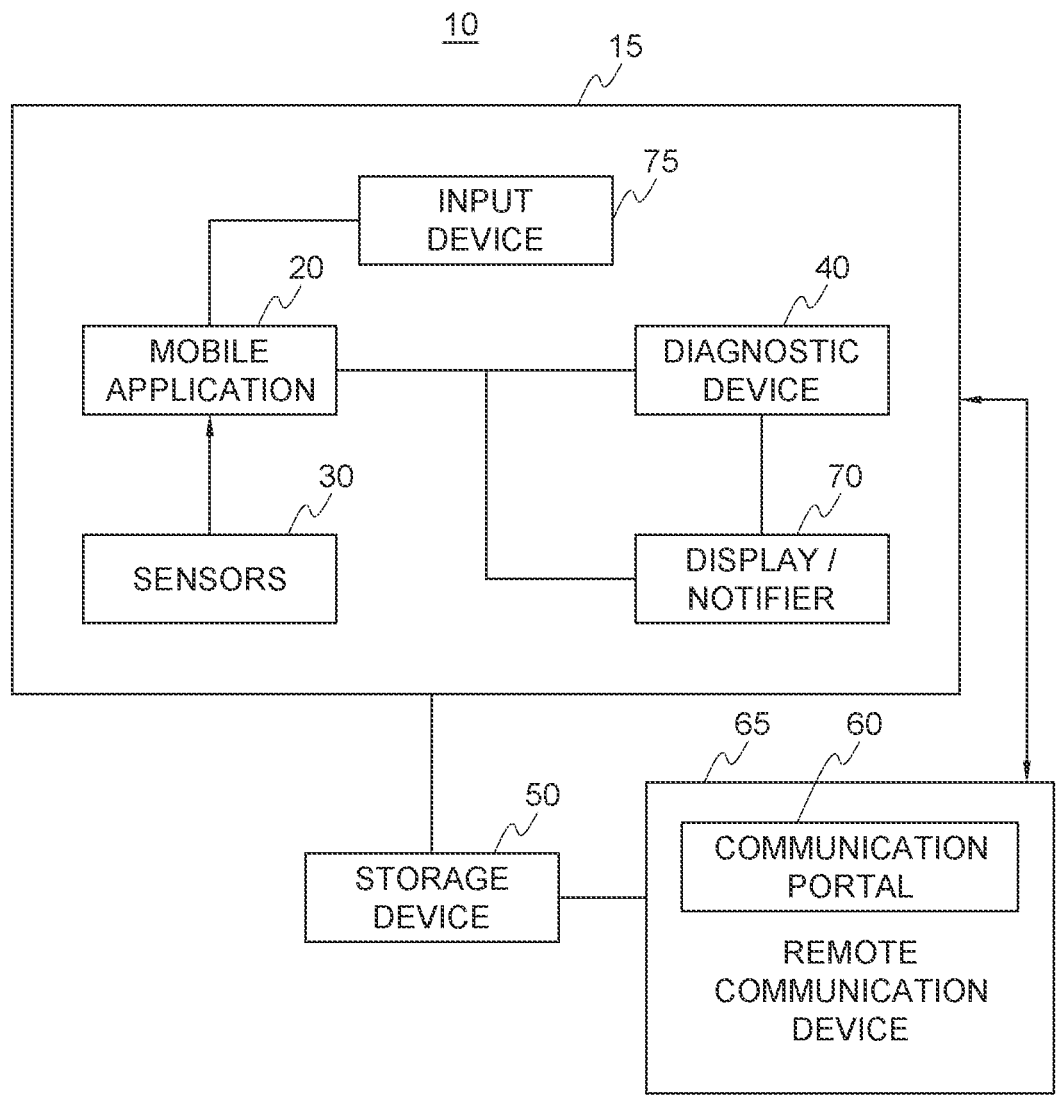
FIG. 1 discloses a block diagram illustrating an embodiment of a system for data capture, classification, and presentation based on information obtained from a user wearing a measuring device and using a mobile application.

Reference will be made below in detail to embodiments, non-limiting examples of which are illustrated in the accompanying drawings. Wherever possible, the same reference numerals used throughout the drawings refer to the same or like parts.

Embodiments solve problems in the art by providing a method and system for collecting, classifying, and presenting data on physiological and psychological states either in a controlled setting such as a laboratory or clinic, or in a natural environment, by which is meant the setting of ordinary daily human activities (outside a lab or clinic) where stimulus and engagements in the environment are not controlled or artificially manufactured, but instead occurs randomly based on other uncontrolled stimulus in the environment where the uncontrolled stimulus is unpredictable. Thus, in the natural environment, events or stimuli which may adversely affect the physiological or psychological state of an individual or user are unknown in advance and are not necessarily being controlled by the individual or another individual or entity, as such events are simply occurring as they normally would.

Persons skilled in the art will recognize that an apparatus, such as a data processing system, including a CPU, memory, I/O, program storage, a connecting bus, and other appropriate components, could be programmed or otherwise designed to facilitate the practice of a method of an embodiment. Such a system would include appropriate program means, or as disclosed herein, mobile application, for executing the method.

Broadly speaking, a purpose of embodiments disclosed herein is to provide a data collection and classification system based on information obtained from a user using sensors embedded in a mobile device and a mobile application to evaluate data that may be collected in a natural environment, and/or in a more controlled environment such as a lab or clinic. The mobile device may be any device that a user may have in possession such as, but not limited to, a mobile phone, smartphone, wearable device, computing tablet, etc.

The resulting classification is communicated to the user where notification may include information to exercise or techniques to bring the classification to an acceptable level if the classification exceeds a predefined threshold. To facilitate an understanding of the embodiments disclosed herein, it is described hereinafter with reference to specific implementations thereof. Embodiments may be described in the general context of computer-executable instructions, such as program modules, being executed by any device such as, but not limited to, a computer, designed to accept data, perform prescribed mathematical and/or logical operations usually at high speed, where results of such operations may or may not be displayed. Generally, program modules include routines, programs, objects, components, data structures, etc., that perform particular tasks or implement particular abstract data types. As used herein, such program modules may be collectively referred to as a mobile application. As a non-limiting example, software programs that underlie embodiments can be coded in different programming languages, for use with different devices, or platforms. It will be appreciated, however, that the principles that underlie embodiments disclosed herein can be implemented with other types of computer software technologies, as well.

Moreover, those skilled in the art will appreciate that embodiments disclosed herein may be practiced with other computer system configurations, multiprocessor systems, microprocessor-based or programmable consumer electronics, minicomputers, mainframe computers, and the like. Embodiment may also be practiced in distributed computing environments where tasks are performed by remote processing devices that are linked through at least one communications network. In a distributed computing environment, program modules may be located in both local and remote computer storage media including memory storage devices.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Referring now to the drawings, embodiments will be described. Embodiments can be implemented in numerous ways, including as a system (including a computer processing system), a method (including a computerized method), an apparatus, a computer readable medium, a computer program product, a computer software code, or a data structure tangibly fixed in a computer readable memory. Several embodiments, illustrating non-limiting examples, are discussed below.

As used herein, physiological and psychological ("physiological/psychological") states may include a determination of at least one of stress, anxiety, anger, panic, or depression. Physiological or biological stress may be considered a user's response to a stressor such as an environmental condition or a stimulus. Stress is a body's method of reacting to a challenge. According to the stressful event, the body's way to respond to stress is by sympathetic nervous system activation which results in the fight-or-flight response. In humans, stress typically describes a negative condition or a positive condition that can have an impact on a person's mental and physical well-being. Anxiety is associated with chronic fear, worry, and stress strong enough to interfere with an individual's activities of daily living. Panic is associated with strong acute fear, worry, anxiety and stress. Depression is characterized by depressed mood and loss of interest in normal activities, causing impairments in daily life. Anger is an emotional state associated with a strong uncomfortable response to perceived provocation or threat and is associated with a biological stress response. Each of these states is associated with specific behavioral changes that can be measured continuously and passively by sensors embedded in mobile devices, leveraging features such as audio waveforms, user movement, online activities, and device interactions. The embodiments below disclose non-limiting examples that are not limited to a laboratory or confined location such as, but not limited to, an examination room. As should be appreciated, events triggering adverse physiological/psychological states are unpredicted as they may occur in the current environment where the user is located. The embodiments disclosed herein provide for being able to ascertain when adverse physiological/psychological states are experienced regardless of the location of the user as sensors to measure characteristics of the user and device to evaluate the characteristics to determine adverse physiological or psychological states are available for mobility and ease of use as the sensors are in the possession of the user.

"Adverse physiological/psychological states" may be determined based on a measurement or level associated with the physiological/psychological state that is either preset as a standard for any user or calibrated to a specific user based on prior measurements taken from the user. Thus, the term "adverse" is not provided as a vague term, but is used to classify when the physiological/psychological state is determined to be at a level or amount that is affecting a performance of the user.

A system is designed to improve an individual's overall mental health and wellness as well as the quality and efficiency of therapy of an individual by substantially increasing a medical provider's insight into adverse physiological or psychological states events experienced by the individual, or patient, during treatment. Though the terms "medical provider" and "patient" are used, these terms are not provided to be limiting. The relation can be any relationship such as, but not limited to, peer to peer, employer to employee, teacher to student, parent to child, or used individually. Such insight may include real-time data on adverse physiological/psychological states, triggers of physiological/psychological state, mitigations employed, and physiological/psychological response is captured and summarized for the patient. Thus, embodiments disclosed herein may be used in isolation and/or in support of ongoing treatment or training to improve tracking, effectiveness, and efficiency of treatment or performance.

FIG. 1 discloses a block diagram illustrating an embodiment of a system for data capture, classification, and presentation based on information obtained from users wearing a measuring device and using a mobile application. As illustrated in FIG. 1, the system 10 may incorporate a mobile application 20, sensors 30 embedded in a mobile device 15 such as, but not limited to, a mobile phone and a diagnostic device 40. The mobile application 20, in conjunction with the phone-embedded sensors 30, wherein at least one sensor 30 may be utilized, may track and assess physiological and contextual indicators of events such as, but not limited to, stress, anxiety, anger, panic, or depression, capture subjective emotional states and triggers associated with these events, deliver biofeedback to users to increase awareness of non-optimal arousal states, and trigger real-time evidence-based strategies for addressing adverse physiological/psychological states. A diagnostic device 40 is also disclosed. The diagnostic device 40 may compare real-time physiological/psychological data to pre-determined baseline levels to indicate times when a given threshold is exceeded, thus indicating adverse physiological/psychological states.

Determination of physiological/psychological states may be evaluated over a given period of time. The period of time may be real-time or near real-time, as non-limiting examples. Other extended time periods may also be used. As used herein, "real-time" or "near real-time" may be based on a predetermined comparison schedule such as, but not limited to, a second-to-second comparison, minute-to-minute comparison, or hour-to-hour comparison. Thus, in general, real-time or near real-time may be based on a second, minute or hour or any variation of time as its time period. Thus, as explained, the comparison period may be any defined period including, but not limited to seconds, multiple minutes, hourly, etc. As such, the sensor device 30 may be able to collect data within this selected period of time. As such, as a non-limiting example, an accelerometer, a non-limiting example of a sensor 30, may have a minimum sampling rate of approximately 32 Hertz ("Hz").

As further illustrated in FIG. 1, information or data collected may be communicated to a storage device 50 such as, but not limited to, a remote storage device, including, but not limited to, a secure cloud server. Therefore, the further use of secure cloud server herein should not be considered limiting. In a non-limiting example, the information or data collected may be stored for comparing recently acquired information with information or data acquired previously. As a non-limiting example, the mobile application 20 may also support reminders such as, but not limited to, treatment reminders, from a peer, coach, employer, medical provider such as, but not limited to, a counselor, psychologist, psychiatrist, etc. Thus, as discussed above, the provider of reminders may be the user or another individual such as, but not limited to, a parent, teacher, etc. Such reminders may be accomplished by providing a communication portal 60 such as, but not limited to, a web-based provider portal through which the provider may review the data in the server 50. In an embodiment, the mobile application 20 may provide biofeedback of physiological state to increase awareness of the onset of adverse physiological/psychological states, provide the user with options to individually select treatment techniques or suggest individualized evidence-based treatment techniques such as, but not limited to, deep breathing exercises, biofeedback exercises, relaxation, reflection, or journaling, designed to reduce symptoms of adverse physiological or psychological states the user is experiencing, and send data wirelessly.

Thus, the portal 60 provides two-way communication, since the provider is able to monitor data collected, stress incidents, and provide directions to the user from a remote communication device 65 such as, but not limited to, a computer terminal, mobile device or similar computing mechanism. As a non-limiting example, if a recurring level of stress is above a certain threshold, the provider may send a message from the remote computer terminal 65, mobile device 65, etc., to the system 10, which may appear as a text message through a display or notifier 70 of the system or wearable measuring device 10, visible or audible to the user. The display or notifier 70 may provide for at least one of visual, audible, and tactile information being provided to the user. In another non-limiting example, the message may be communicated to a mobile phone 10 which may operate in conjunction with the embedded sensors 30. In a non-limiting example, the secure cloud server 50 may be a part of the mobile phone 10 or located at a second mobile phone.

As will be explained further herein, the system 10 may further comprise an entry, input or user interface, device 75 through which the user may acknowledge, or designate, when the user is experiencing the adverse physiological/psychological state. The entry device 75 may be located on the mobile device 15 or a wearable measuring device remote from the mobile device that may be used in association with the mobile device. In a non-limiting example, the wearable measuring device could be a smart watch, fitness band, smart glasses, smart material, etc., which is wirelessly in communication with a mobile device such as, but not limited to, a mobile phone.

Figure 2:
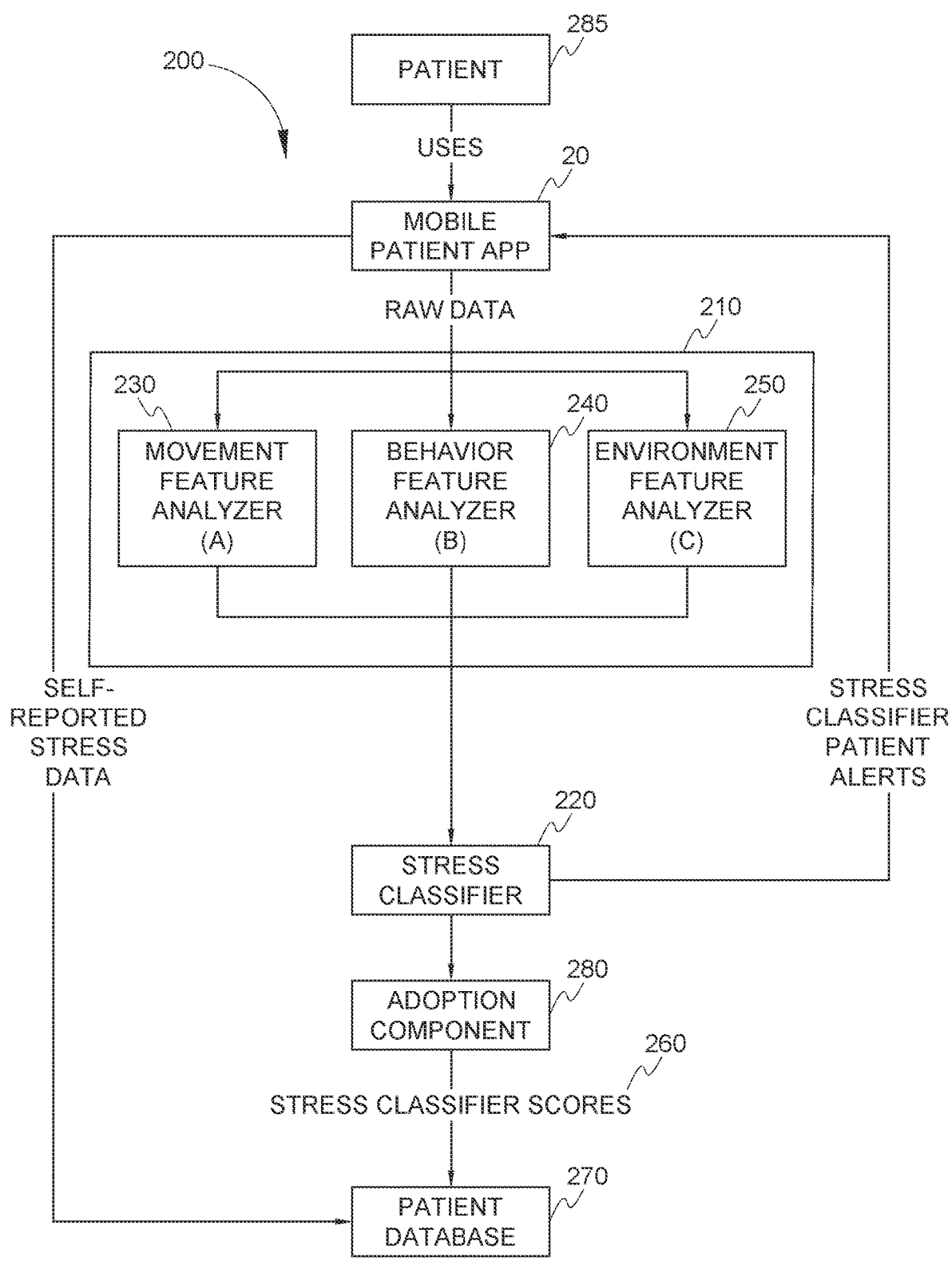
FIG. 2 discloses a block diagram illustrating an embodiment of a system for data capture, classification, and presentation based on information obtained from a user.

FIG. 2 shows an embodiment of an adverse physiological or psychological state classification system. The user, patient, or subject using the mobile patient application 20 may monitor their physiological or psychological state, in real-time, near real-time, or at another defined interval as discussed herein. In a non-limiting example, the mobile patient application 20 may reside on a mobile device such as, but not limited to, a mobile phone (smartphone), watch or tablet, etc., where the user may use the mobile device to monitor their physiological or psychological state.

As a non-limiting example, the mobile patient application 20 may implement two components for classifying the patient's physiological/psychological state based on a define timed basis. A first component may be a physiological/psychological state feature analyzer 210 which may read in a pre-defined block of raw sensor data such as, but not limited to, read every minute, and output a set of physiological/psychological state features based on that epoch of data. Such features include, but are not limited to, audio waveforms, user movement, online activities, and device interactions. A second component may be a physiological/psychological state classifier 220 that may read the features determined by different analyzers 230, 240, 250, provided from the physiological/psychological state feature analyzer 210 and may output a physiological/psychological state classifier score, magnitude or level 260 to a patient database 270, which may be located on the secure cloud server 50, which may keep track of either the patient's self-reported physiological/psychological state(s) and classifier-reported physiological/psychological state(s) while the mobile patient application 20 and phone-embedded sensors 30 are being used, and may also output alerts to the patient when some threshold level of stress, anxiety, anger, panic, or depression occurs.

In an embodiment, in operation, the system 10 may first be trained by the user or wearer running a calibration phase where the user may sit quietly and relax, allowing the sensors 30 to capture the user's baseline physiological and psychological levels, including a user's normal level of movement and activity. During normal operation, the classifier 220 may make a determination of physiological/psychological state relative to these baseline references. In addition, the physiological/psychological state classifier 220 may contain an adaptation or adopting component 280, which may be, but is not limited to being, an adaptation algorithm, that permits discrepancies in self-reported physiological/psychological state, entered using the user interface 75 on the mobile device 15, and classifier-reported physiological/psychological state to reset a bias/threshold in the constituent classifiers allowing lesser or greater sensitivity to movement and behavior signals. The result is a physiological/psychological state classifier with some capacity to adapt its sensitivity to particular individuals.

Data collection from the phone-embedded sensor array 30 may be done via the mobile patient application 20. Based on the sensors 30, one data modality may include accelerometer signals, which indicate the direction of acceleratory motion of the device. Other data modalities may include mobile phone event log signals, which indicate the applications used by a user and screen interaction signals (e.g., touch, pressure, duration, etc.) which may indicate how a user interacts physically with the mobile phone screen, environmental signals which may indicate the ambient light and sound environment of the user, and location signals such as global positioning system information. Samples from these sensors may be uniformly or non-uniformly sampled. The data collection process may merely bundle the samples into (non-overlapping) minute, or another time phrase as discussed above, blocks to allow feature analysis over a defined time period basis.

FIG. 2 further shows a flow of information or data within the system. As shown, information is obtained from the user or patient 285 and is passed to the mobile application 20. Within the mobile application the physiological/psychological state feature analyzer 210 resides. The physiological/psychological state feature analyzer 210 has at least a movement feature analyzer 230, a behavior feature analyzer 240 and an environment feature analyzer 250. Information from the physiological/psychological state feature analyzer 210 is then passed to the physiological/psychological state classifier 220 which produces a physiological/psychological state classifier score 260. This score is passed to the database 270 which may be located at the storage device 50 which may be remote. As is also shown, the physiological/psychological state classifier output may also be reported to the mobile application 20 for viewing by the user on the display 70. As used herein, "output" may be a magnitude, score, or another determinator that provides information to the user. Also, the user may use the mobile application by way of the input device 75 to self-report physiological/psychological state data to the database 270.

Figure 3:
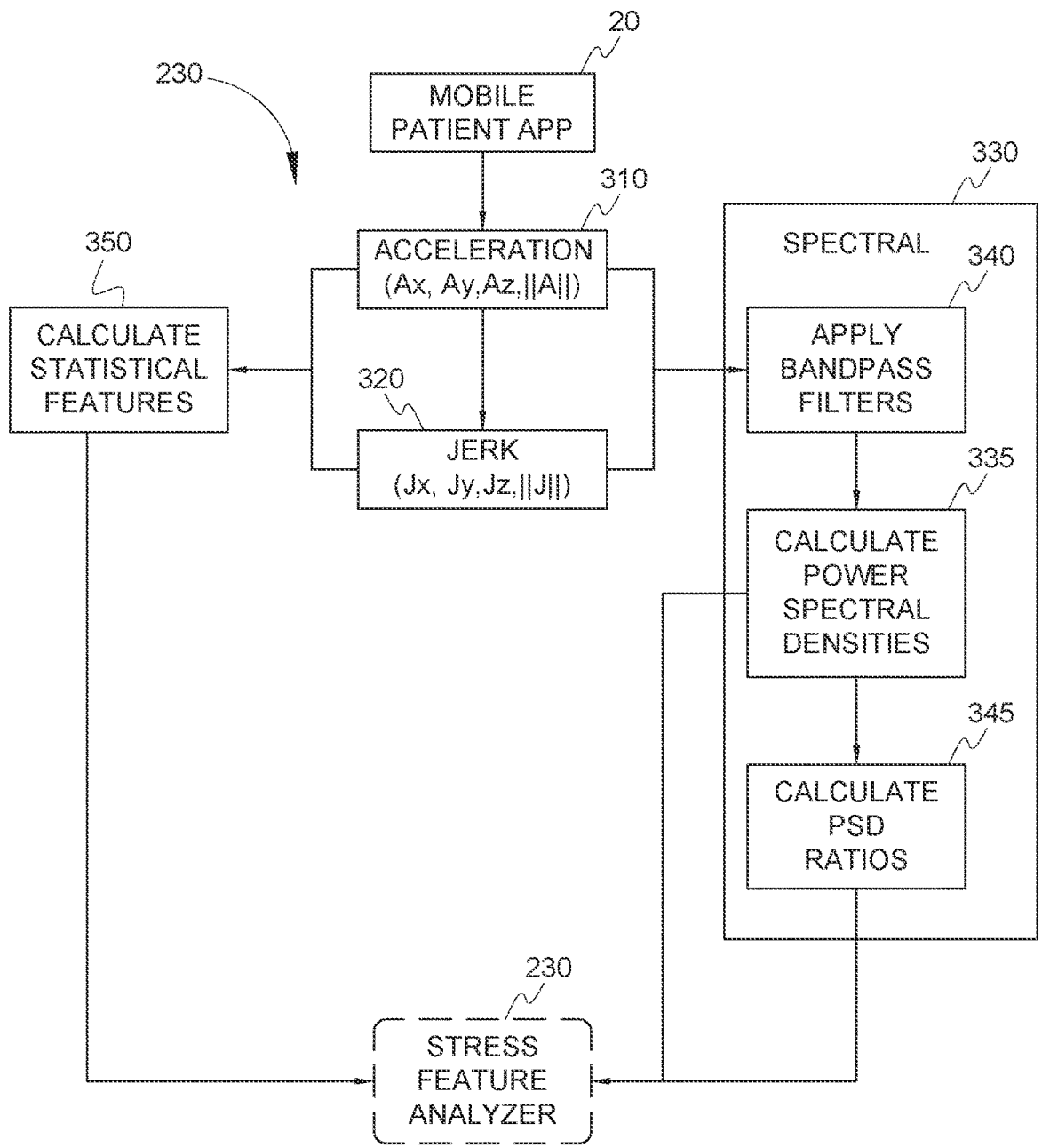
FIG. 3 shows a flowchart illustrating an embodiment of an overview of information flow for movement feature extraction.

FIG. 3 shows an embodiment of the movement feature analyzer. As illustrated in FIG. 2, there may be three parallel channels of feature extraction in the stress feature analyzer 210 that read in raw samples for, respectively, triaxial (i.e., x, y, z) acceleration (A), behavioral signals (B), and environmental signals (C). Each channel A, B, C is explained in further detail below.

As disclosed above, the movement feature analyzer 230 may be used to extract information from raw data collected via a triaxial accelerometer 30. These features may be used for classifying physiological/psychological states. This analyzer 230 may extract movement features according to, but not limited to, the steps described below.

The feature extraction process for movement analyzer 230 may have a first step of movement feature extraction 310 that may convert all of the multi-axis accelerations detected during a specific time period, such as the minute into a measure of magnitude of movement. If the accelerations $a_x$, $a_y$, and $a_z$ at a given time are given in terms of the units of the gravitational acceleration constant g, then the magnitude of acceleration, $\|a\|$, is defined as:

$$\|a\| = \left| \sqrt{a_x^2 + a_y^2 + a_z^2} - 1.0 \right|$$

This means that the Euclidean norm of the acceleration vector is taken and, effectively, g is subtracted out leaving the non-gravitational component of the acceleration. This signal may be rectified (i.e., absolute value taken) in order to treat accelerations in either direction as being positive instances of movement.

A second step of movement feature extraction 320 may be to calculate jerk (i.e., the first derivative of acceleration with respect to time) for the accelerations $a_x$, $a_y$, $a_z$, and $\|a\|$.

A third step of movement feature extraction 330 may be to calculate spectral features of movement, or spectral determination 330, such as the power spectral density 335 in specific frequency bands, wherein bandpass filters 340 are applied, for acceleration and jerk. These may include a low-frequency band (e.g., 0.01-0.1 Hz), a middle-frequency band (e.g., 0.1-0.5 Hz), a high-frequency band (e.g., 0.1-1 Hz), a very-high-frequency band (e.g., 1-2 Hz), and an ultra-high frequency band (e.g., 2-10 Hz). These may also include ratios, e.g., between power spectral density in the high-frequency and low-frequency bands.

A fourth step of movement feature extraction 350 may be to calculate statistical features of acceleration and jerk. These may include mean, maximum, minimum, median, standard deviation, energy, skewness, and kurtosis.

Figure 4:
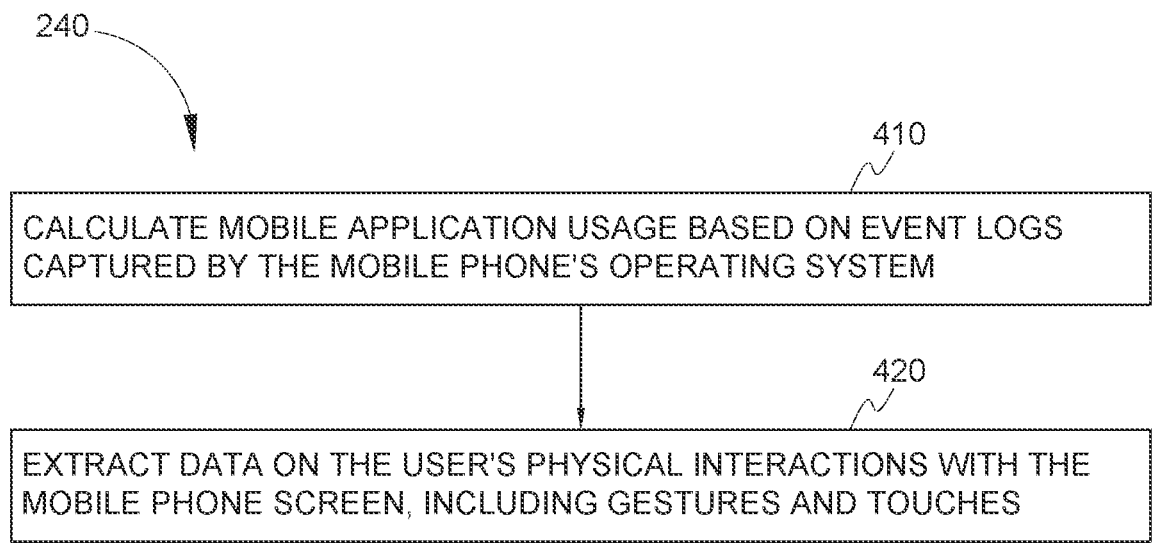
FIG. 4 shows an embodiment of the behavior feature analyzer.

FIG. 4 shows an embodiment of the behavior feature analyzer. The behavior feature analyzer 240 may be used to extract information from raw data collected from sensors embedded in a mobile device. These features may be used for classifying physiological/psychological states. This analyzer may extract behavioral features according to, but not limited to, the steps described below.

A first step of behavior feature extraction may be to calculate mobile application usage based on event logs captured by the mobile phone's operating system, at 410.

A second step of behavior feature extraction may be to extract data on the user's physical interactions with the mobile phone screen, including gestures and touches, at 420.

Figure 5:
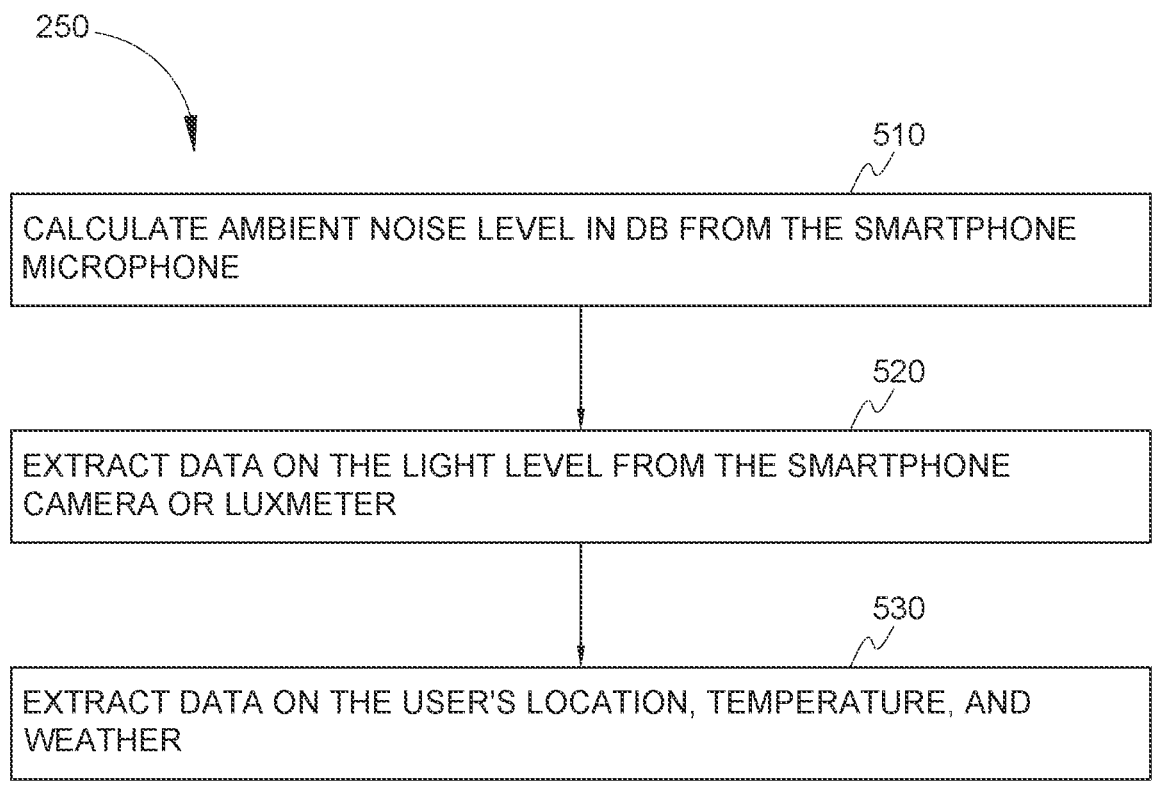
FIG. 5 shows an embodiment of the environmental feature analyzer.

FIG. 5 shows an embodiment of the environmental feature analyzer. The environmental feature analyzer 250 may be used to extract information from raw data collected from sensors embedded in a mobile device. These features may be used for classifying physiological/psychological states. This analyzer may extract environmental features according to, but not limited to, the steps described below.

A first step of environmental feature extraction may be to calculate ambient noise level in dB from the smartphone microphone, at 510.

A second step of environmental feature extraction may be to extract data on the light level from the smartphone camera or luxmeter, at 520.

A third step of environmental feature extraction may be to extract data on the user's location, temperature, and weather, at 530.

Figure 6:
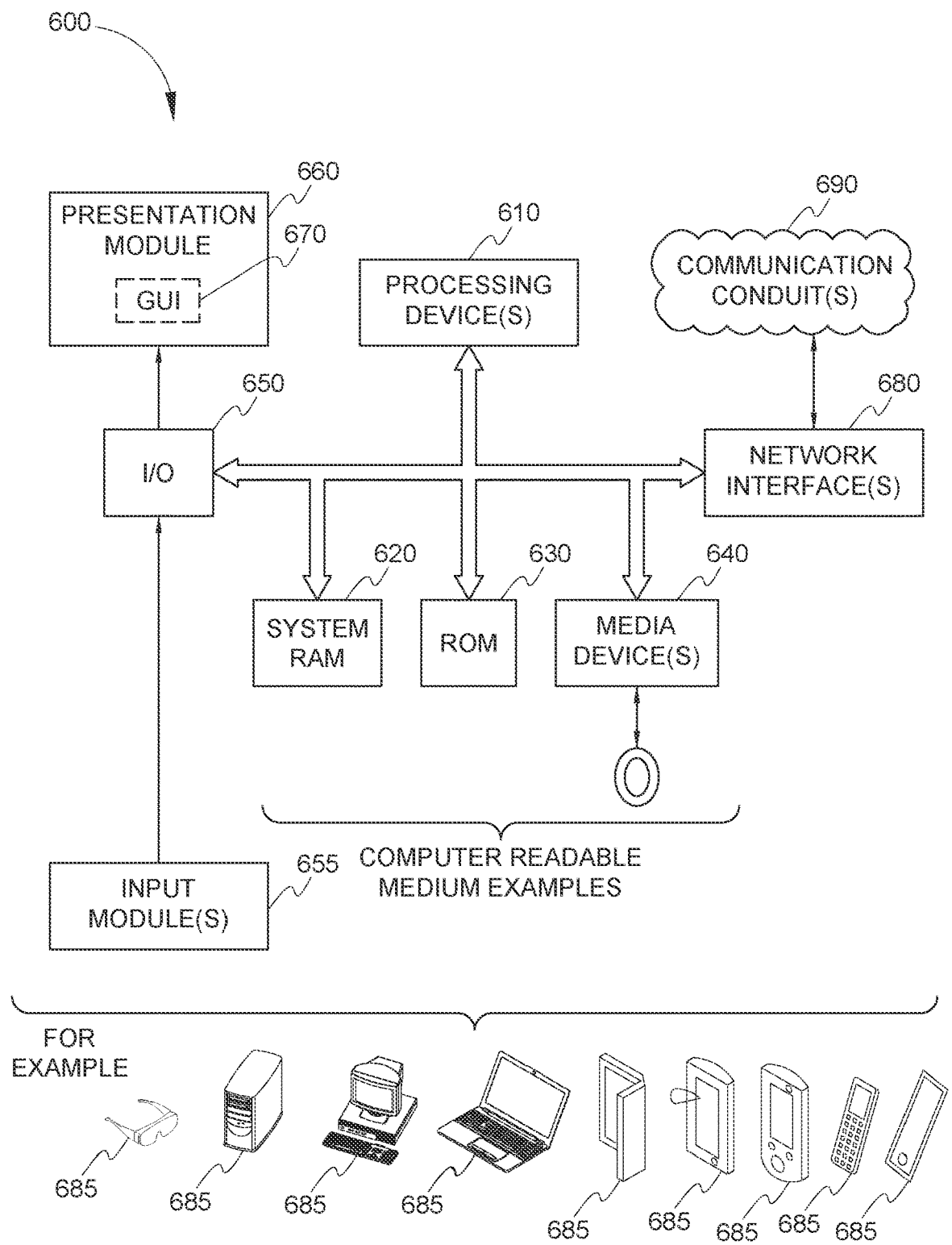
FIG. 6 shows a basic configuration of a computing device which may include any type of stationary computing device or a mobile computing device.

Referring now to FIG. 6, in a basic configuration, a computing device, or system, may include any type of stationary computing device or a mobile computing device. The computing device 600 may include one or more processors 610 and system memory in a hard drive. Depending on the exact configuration and type of computing device, system memory may be volatile (such as RAM) 620, non-volatile (such as read only memory (ROM) 630, flash memory, and the like) or some combination of the two. A system memory 620, 630 may store an operating system, one or more applications, and may include program data for performing flight, navigation, avionics, power managements operations such as for space operations.

The computing device 600 may carry out one or more blocks of a process described herein. The computing device 600 may also have additional features or functionality. As a non-limiting example, the computing device 600 may also include additional data storage devices (removable and/or non-removable) 640 such as, for example, magnetic disks, optical disks, or tape. The computer storage media 640 may include volatile and non-volatile, non-transitory, removable and non-removable media implemented in any method or technology for storage of data, such as computer readable instructions, data structures, program modules or other data. The system memory 620, 630, removable storage and non-removable storage 640 are all non-limiting examples of computer storage media. The computer storage media may include, but is not limited to, RAM, ROM, Electrically Erasable Read-Only Memory (EEPROM), flash memory or other memory technology, compact-disc-read-only memory (CD-ROM), digital versatile disks (DVD) or other optical storage, magnetic cassettes, magnetic tape, magnetic disk storage or other magnetic storage devices, or any other physical medium which can be used to store the desired data and which can be accessed by computing device. Any such computer storage media may be part of device.

The computing device may also include or have interfaces 650 for input device(s) (not shown) such as a keyboard, mouse, pen, voice input device, touch input device 75, etc. The computing device 600 may include or have interfaces 655 for connection to output device(s) such as a display, speakers, etc. The computing device 600 may include a peripheral bus for connecting to peripherals. Computing device may contain communication connection(s) 690 that allow the device to communicate with other computing devices 685, such as over a network or a wireless network, such as, but not limited to between Bluetooth® connected devices, etc. By way of example, and not limitation, communication connection(s) 690 may include wired media such as a wired network or direct-wired connection, and wireless media such as acoustic, radio frequency (RF), infrared, Bluetooth® and other wireless media. The computing device may include a network interface card 680 to connect (wired or wireless) to a network. The computing device 600 may also provide for a presentation module 660, which also may have a graphical user interface (GUI) 670. The presentation module 660 and GUI 670 may provide information to the computing device 685, as discussed above, through which the presentation module 660 and/or GUI 670 is accessible or viewable via the computing device 685.

Computer program code for carrying out operations described above may be written in a variety of programming languages, including but not limited to a high-level programming language, such as C or C++, for development convenience. In addition, computer program code for carrying out operations of embodiments described herein may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed Digital Signal Processor (DSP) or microcontroller. A code in which a program of the embodiments is described can be included as a firmware in a RAM, a ROM and a flash memory. Otherwise, the code can be stored in a tangible computer-readable storage medium such as a magnetic tape, a flexible disc, a hard disc, a compact disc, a photo-magnetic disc, a digital versatile disc (DVD).

The embodiments may be configured for use in a computer or a data processing apparatus which includes a memory, such as a central processing unit (CPU), a RAM and a ROM as well as a storage medium such as a hard disc.

The "step-by-step process" for performing the claimed functions herein is a specific algorithm, and may be shown as a mathematical formula, in the text of the specification as prose, and/or in a flow chart. The instructions of the software program create a special purpose machine for carrying out the particular algorithm. Thus, in any means-plus-function claim herein in which the disclosed structure is a computer, or microprocessor, programmed to carry out an algorithm, the disclosed structure is not the general-purpose computer, but rather the special purpose computer programmed to perform the disclosed algorithm.

A general-purpose computer, or microprocessor, may be programmed to carry out the algorithm/steps for creating a new machine. The general-purpose computer becomes a special purpose computer once it is programmed to perform particular functions pursuant to instructions from program software of the embodiments described herein. The instructions of the software program that carry out the algorithm/steps electrically change the general-purpose computer by creating electrical paths within the device. These electrical paths create a special purpose machine for carrying out the particular algorithm/steps.

Thus, as disclosed herein, embodiments relate to a system, method, and computer program product for continuous classification of physiological/psychological states in a mobile environment from features derived directly from smartphone sensors. The system comprises a measuring device comprising at least one sensor configured to collect data from a user based on the sensor being embedded in a mobile device. When users experience an adverse physiological/psychological state, their behavior changes in ways that include, but are not limited to, abnormal patterns of movement, and changes in device usage and user interaction. The system further collects motion, position, and location data from users' smartphones and analyzes it in real-time to detect these patterns. The system also comprises a physiological/psychological state classifier configured to classify and report stress based on a Random Forest classifier trained using these features, which achieves 95% accuracy in classifying epochs of at least one of stress, anxiety, anger, panic, or depression.

The method comprises collecting, in real-time, from a plurality of sensors configured to collect data about a user of the mobile phone based on the plurality of sensors collecting information about movement and behavior of the user in possession of the mobile phone The method further comprises identifying, in real-time, when the user experiences adverse physiological/psychological states based on a movement and behavior feature analyzer configured to an determine out-of-the-ordinary movement pattern made by the user based on at least one of data collected about a motion experienced by the mobile phone and data collected about a geographic location of the mobile phone. The method also comprises classifying, in real-time, a user's adverse physiological/psychological state based on the out-of-the-ordinary movement or behavior of the user and report the level of at least one of stress, anxiety, anger, panic, or depression experienced by the user based on at least one of data collected about the motion experienced by the mobile phone and data collected about the geographic location of the mobile phone. Finally, the system comprises a notifier to provide, in real-time, at least one of an audible notification, a tactile notification, and a visual notification that the user is experiencing an adverse physiological/psychological state, wherein the notifier further prompts the user to utilize at least one of a resource available within the mobile phone and a technique to mitigate the effects of that adverse state such as, but not limited to, deep breathing exercises, biofeedback exercises, relaxation, reflection, or journaling.

The computer program product is a non-transitory processor readable storage medium, providing an executable computer program product, the executable computer program product comprising a computer software code. When executed on a processor, the code causes the processor to identify, in real-time, when an adverse physiological/psychological state is experienced by the user based on an analysis of temporal domain metrics and frequency domain metrics based on at least one of a mean, maximum, minimum, median, standard deviation, energy, skewness, amplitude, magnitude, kurtosis, and time duration of the data collected about the motion, behavior, and environment experienced by the mobile phone and the data collected about the geographic location of the mobile phone. The processor is also caused to cease to identify, in real-time, when the level of stress, anxiety, anger, panic, or depression exceeds a predefined threshold. The processor is also caused to classify, in real-time, the level of at least one of stress, anxiety, anger, panic, or depression experienced, and report at least to the user when an adverse physiological/psychological state is experienced. The system may provide tools for users to help mitigate or otherwise prevent the effects of at least one of stress, anxiety, anger, panic, depression, and other adverse physiological/psychological states such as, but not limited to, deep breathing exercises, biofeedback exercises, relaxation, reflection, or journaling. These mitigations may include: audio media, such as recordings of guided meditation exercises or relaxing sounds; visual media, such as relaxing images; interactive exercises, such as biofeedback, where users are instructed to consciously relax and may alter the user's physiological status as physiological information is displayed, or provided, to the user in real or near real-time via the mobile device user interface; and educational resources on topics including, but not limited to, stress, anger, anxiety, panic, depression, and sleep.

In another embodiment, as disclosed above, a non-transitory, tangible computer-readable storage medium having instructions stored thereon that, if executed by a computing system with one or more processors, causes the computing system to perform operations disclosed above with respect to the computer implemented method discussed above.

Unless otherwise defined, all terms (including technical and scientific terms) used herein have the same meaning as commonly understood by one of ordinary skill in the art to which embodiments belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In particular, unless specifically stated otherwise as apparent from the discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such data storage, transmission or display devices.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order or importance, but rather the terms first, second, etc., are used to distinguish one element from another. As used herein the expression "at least one of A and B," will be understood to mean only A, only B, or both A and B.

While various disclosed embodiments have been described above, it should be understood that they have been presented by way of example only, and not limitation. Numerous changes, omissions and/or additions to the subject matter disclosed herein can be made in accordance with the embodiments disclosed herein without departing from the spirit or scope of the embodiments. Also, equivalents may be substituted for elements thereof without departing from the spirit and scope of the embodiments. In addition, while a particular feature may have been disclosed with respect to only one of several implementations, such feature may be combined with one or more other features of the other implementations as may be desired and advantageous for any given or particular application. Furthermore, many modifications may be made to adapt a particular situation or material to the teachings of the embodiments without departing from the scope thereof.

Further, the purpose of the foregoing Abstract is to enable the U.S. Patent and Trademark Office and the public generally and especially the scientists, engineers and practitioners in the relevant art(s) who are not familiar with patent or legal terms or phraseology, to determine quickly from a cursory inspection the nature and essence of this technical disclosure. The Abstract is not intended to be limiting as to the scope of the present disclosure in any way.

Therefore, the breadth and scope of the subject matter provided herein should not be limited by any of the above explicitly described embodiments. Rather, the scope of the embodiments should be defined in accordance with the following claims and their equivalents.

We claim:

1. A system comprising:
a mobile device having a processor and a plurality of sensors, at least one sensor of the plurality of sensors as part of the mobile device, in communication with the mobile device configured to collect data about a user in possession of the mobile device based on at least one of the plurality of sensors collecting information about movement of the user in possession of the mobile device;
a movement feature analyzer configured to determine out-of-ordinary movement pattern relative to a preset standard made by the user based on at least one of data collected about a motion experienced by the mobile device and data collected about a geographic location of the mobile device, the movement feature analyzer comprising instructions which when executed by the processor causes the processor to determine temporal domain metrics and frequency domain metrics based on at least one of a mean, maximum, minimum, median, standard deviation, energy, skewness, amplitude, magnitude, kurtosis, and time duration of the at least one of the data collected about the motion experienced by the mobile device and the data collected about the geographic location of the mobile device;
a physiological/psychological state classifier configured to classify a physiological/psychological state of the user based on the determined out-of-ordinary movement pattern of the user and report at least one of a magnitude and a level of the physiological/psychological state experienced by the user based on at least one of the data collected about the motion and the data collected about the geographic location of the mobile device, the physiological/psychological state classifier comprising instructions, which when executed by the processor, cause the processor to apply prior results to newly collected data to classify the physiological/psychological state into at least one of a physiological/psychological state level and a physiological/psychological state magnitude and to apply at least one of acceleration information, jerk movement information and spectral features of movement information to the newly collected data to classify the physiological/psychological state into the physiological/psychological state level; and
a notification device to provide at least one of an audible notification, a tactile notification and a visual notification that the user is experiencing a physiological/psychological state measured on the at least one of the physiological/psychological state level and the physiological/psychological state magnitude, wherein the notification device further prompts the user to utilize at least one of a resource available within the mobile device and a technique to reduce the at least one of the physiological/psychological state level and the physiological/psychological state magnitude of an adverse physiological/psychological state,
wherein the adverse physiological/psychological state includes one of anxiety, anger, panic, and depression.

2. The system according to claim 1, further comprising a collection device to maintain data about the physiological/psychological state classified including at least one of when the physiological/psychological state is classified, a location of the mobile device when the physiological/psychological state is classified, and a frequency of the physiological/psychological state occurring.

3. The system according to claim 2, further comprising a database that is at least one of remote and within the mobile device, wherein the collection device provides the physiological/psychological state to the database.

4. The system according to claim 1, wherein the physiological/psychological state level is determined based on a specific time interval.

5. The system according to claim 1, wherein the notification device utilizes at least one of a display of the mobile device, an audible subsystem of the mobile device and a tactile notification system of the mobile device to provide the physiological/psychological state level of the user.

6. The system according to claim 5, wherein the notification device utilizes at least one of the display of the mobile device, the audible subsystem of the mobile device and the tactile notification system of the mobile device to prompt the user to utilize at least one of a resource and a physiological/psychological state reduction technique to reduce the physiological/psychological state level.

7. The system according to claim 1, further comprising a behavior feature analyzer configured to determine behavior of the user based on at least one of data collected event logs captured by the mobile device and data collected about physical interactions of the user at a user interface of the mobile device, the behavior feature analyzer comprising instructions, which when executed by the processor, cause the processor to determine usage of the mobile device by the user based on the event logs captured by the mobile device and user interaction with an input device of the mobile device to determine a behavior; and wherein the physiological/psychological state classifier is further configured to classify the physiological/psychological state level based on behavior of the user determined by the event logs and the physical interactions with the mobile device, the physiological/psychological state classifier further comprising instructions, which when executed by the processor, cause the processor to compare newly acquired information about mobile application usage based on the event logs and the physical interactions of the user with the mobile device to apply prior results to the newly collected data to classify the physiological/psychological state into the physiological/psychological state level.

8. The system according to claim 1, further comprising an environmental feature analyzer configured to determine environmental information of where the mobile device is located, the environmental feature analyzer comprising instructions, which when executed by the processor, cause the processor to determine at least one of an ambient noise level, light level, weather conditions, and temperature; and wherein the physiological/psychological state classifier is further configured to classify, in real-time, the physiological/psychological state level based on at least the one of an ambient noise level, light level, weather conditions, and temperature to apply prior results to the newly collected data to classify the physiological/psychological state into the physiological/psychological state level.

9. A system comprising:
a mobile device having a processor and a plurality of sensors, at least one sensor of the plurality of sensors as part of the mobile device, in communication with the mobile device configured to collect data about a user in possession of the mobile device based on at least one of the plurality of sensors collecting information about movement of the user in possession of the mobile device;

a movement feature analyzer configured to determine out-of-ordinary movement pattern relative to a preset standard made by the user based on at least one of data collected about a motion experienced by the mobile device and data collected about a geographic location of the mobile device, the movement feature analyzer comprising instructions, which when executed by the processor, cause the processor to determine temporal domain metrics and frequency domain metrics based on at least one of a mean, maximum, minimum, median, standard deviation, energy, skewness, amplitude, magnitude, kurtosis, and time duration of the at least one of the data collected about the motion experienced by the mobile device and the data collected about the geographic location of the mobile device;

a physiological/psychological state classifier configured to classify a physiological/psychological state of the user based on the determined out-of-ordinary movement pattern of the user and report at least one of a magnitude and a level of the physiological/psychological state experienced by the user based on at least one of the data collected about the motion and the data collected about the geographic location of the mobile device, the physiological/psychological state classifier comprising instructions, which when executed by the processor, cause the processor to apply prior results to newly collected data to classify the physiological/psychological state into at least one of a physiological/psychological state level and a physiological/psychological state magnitude;

a behavior feature analyzer configured to determine behavior of the user based on at least one of data collected event logs captured by the mobile device and data collected about physical interactions of the user at a user interface of the mobile device, the behavior feature analyzer comprising instructions, which when executed by the processor, cause the processor to determine usage of the mobile device by the user based on the event logs captured by the mobile device and user interaction with an input device of the mobile device to determine a behavior; and wherein the physiological/psychological state classifier is further configured to classify the physiological/psychological state level based on behavior of the user determined by the event logs and the physical interactions with the mobile device, the physiological/psychological state classifier further comprising instructions, which when executed by the processor, cause the processor to compare newly acquired information about mobile application usage based on the event logs and the physical interactions of the user with the mobile device to apply prior results to the newly collected data to classify the physiological/psychological state into the physiological/psychological state level; and a notification device to provide at least one of an audible notification, a tactile notification and a visual notification that the user is experiencing an adverse physiological/psychological state based on the at least one of the physiological/psychological state level and the physiological/psychological state magnitude.

10. The system of claim 9, wherein the notification device is configured to prompt the user to utilize at least one of a resource available within the mobile device and a technique to reduce the at least one of the physiological/psychological state level and the physiological/psychological state magnitude associated with the adverse physiological/psychological state.

11. The system according to claim 9, wherein the physiological/psychological state level is determined based on a specific time interval.

12. The system according to claim 9, wherein the notification device utilizes at least one of a display of the mobile device, an audible subsystem of the mobile device and a tactile notification system of the mobile device to provide the physiological/psychological state level of the user.

13. A system comprising:

a mobile device having a processor and a plurality of sensors, at least one sensor of the plurality of sensors as part of the mobile device, in communication with the mobile device configured to collect data about a user in possession of the mobile device based on at least one of the plurality of sensors collecting information about movement of the user in possession of the mobile device;

a movement feature analyzer configured to determine out-of-ordinary movement pattern relative to a preset standard made by the user based on at least one of data collected about a motion experienced by the mobile device and data collected about a geographic location of the mobile device, the movement feature analyzer comprising instructions, which when executed by the processor, cause the processor to determine temporal domain metrics and frequency domain metrics based on at least one of a mean, maximum, minimum, median, standard deviation, energy, skewness, amplitude, magnitude, kurtosis, and time duration of the at least one of the data collected about the motion experienced by the mobile device and the data collected about the geographic location of the mobile device;

a physiological/psychological state classifier configured to classify a physiological/psychological state of the user based on the determined out-of-ordinary movement pattern of the user and report at least one of a magnitude and a level of the physiological/psychological state experienced by the user based on at least one of the data collected about the motion and the data collected about the geographic location of the mobile device, the physiological/psychological state classifier comprising instructions, which when executed by the processor, cause the processor to apply prior results to newly collected data to classify the physiological/psychological state into at least one of a physiological/psychological state level and a physiological/psychological state magnitude;

an environmental feature analyzer configured to determine environmental information of where the mobile device is located, the environmental feature analyzer comprising instructions, which when executed by the processor, cause the processor to determine at least one of an ambient noise level, light level, weather conditions, and temperature; and wherein the physiological/psychological state classifier is further configured to classify, in real-time, the physiological/psychological state level based on at least the one of an ambient noise level, light level, weather conditions, and temperature to apply prior results to the newly collected data to classify the physiological/psychological state into the physiological/psychological state level; and a notification device to provide at least one of an audible notification, a tactile notification and a visual notification that the user is experiencing an adverse physiological/psychological state based on the at least one of the physiological/psychological state level and the physiological/psychological state magnitude.

14. The system of claim 13, wherein the notification device is configured to prompt the user to utilize at least one of a resource available within the mobile device and a technique to reduce the at least one of the physiological/psychological state level and the physiological/psychological state magnitude associated with the adverse physiological/psychological state.

15. The system according to claim 13, wherein the physiological/psychological state level is determined based on a specific time interval.

16. The system according to claim 13, wherein the notification device utilizes at least one of a display of the mobile device, an audible subsystem of the mobile device and a tactile notification system of the mobile device to provide the physiological/psychological state level of the user.

17. A system comprising:
a mobile device having a processor and a plurality of sensors, at least one sensor of the plurality of sensors as part of the mobile device, in communication with the mobile device configured to collect data about a user in possession of the mobile device based on at least one of the plurality of sensors collecting information about movement of the user in possession of the mobile device;
a movement feature analyzer configured to determine out-of-ordinary movement pattern relative to a preset standard made by the user based on at least one of data collected about a motion experienced by the mobile device and data collected about a geographic location of the mobile device, the movement feature analyzer comprising instructions which when executed by the processor causes the processor to determine temporal domain metrics and frequency domain metrics based on at least one of a mean, maximum, minimum, median, standard deviation, energy, skewness, amplitude, magnitude, kurtosis, and time duration of the at least one of the data collected about the motion experienced by the mobile device and the data collected about the geographic location of the mobile device;
a physiological/psychological state classifier configured to classify a physiological/psychological state of the user based on the determined out-of-ordinary movement pattern of the user and report at least one of a magnitude and a level of the physiological/psychological state experienced by the user based on at least one of the data collected about the motion and the data collected about the geographic location of the mobile device, the physiological/psychological state classifier comprising instructions, which when executed by the processor, cause the processor to apply prior results to newly collected data to classify the physiological/psychological state into at least one of a physiological/psychological state level and a physiological/psychological state magnitude,
wherein the instructions, which when executed by the processor, cause the processor to apply the prior results to the newly collected data to classify the physiological/psychological state into the physiological/psychological state level further cause the processor to apply at least one of acceleration information, jerk movement information and spectral features of movement information to the newly collected data to classify the physiological/psychological state into the physiological/psychological state level; and
a notification device to provide at least one of an audible notification, a tactile notification and a visual notification that the user is experiencing an adverse physiological/psychological state based on the at least one of the physiological/psychological state level and the physiological/psychological state magnitude.

18. The system of claim 17, wherein the notification device is configured to prompt the user to utilize at least one of a resource available within the mobile device and a technique to reduce the at least one of the physiological/psychological state level and the physiological/psychological state magnitude associated with the adverse physiological/psychological state.

19. The system according to claim 17, wherein the physiological/psychological state level is determined based on a specific time interval.

20. The system according to claim 17, wherein the notification device utilizes at least one of a display of the mobile device, an audible subsystem of the mobile device and a tactile notification system of the mobile device to provide the physiological/psychological state level of the user.

21. The system according to claim 17, further comprising a collection device to maintain data about the physiological/psychological state classified including at least one of when the physiological/psychological state is classified, a location of the mobile device when the physiological/psychological state is classified, and a frequency of the physiological/psychological state occurring.

22. A system comprising:
a mobile phone device, the mobile phone device comprising:
a plurality of embedded sensors configured to collect data, at least one embedded sensor of the plurality of embedded sensors configured to collect movement data about movement of a user in possession of the mobile phone device;
a notification device to provide at least one of an audible notification, a tactile notification and a visual notification to the user; and
a processor configured to:
receive the collected data from the plurality of embedded sensors;
determine an out-of-ordinary movement pattern relative to a preset standard made by the user in possession of the mobile phone device based on at least one of:
i) first data of the collected data representative of a motion experienced by the mobile phone device, and
ii) second data of the collected data representative of a geographic location of the mobile phone device;
report at least one of a magnitude and a level of a physiological/psychological state experienced by the user based on the at least one of the first data and the second data;
classify the physiological/psychological state of the user into at least one of a physiological/psychological state level and a physiological/psychological state magnitude, based on prior results and the collected data;
cause the notification device to generate at least one the audible notification, the tactile notification and the visual notification representative of the classified physiological/psychological state; and
cause the notification device to prompt the user to utilize at least one of a resource available within the mobile phone device and a technique to reduce the at least one of the physiological/psychological state level and the physiological/psychological state magnitude of the physiological/psychological state, in response to the classified physiological/psychological state being an adverse physiological/psychological state based on the determined out-of-ordinary movement pattern.

* * * * *